US007164127B2

(12) United States Patent
Nakagaki et al.

(10) Patent No.: US 7,164,127 B2
(45) Date of Patent: Jan. 16, 2007

(54) SCANNING ELECTRON MICROSCOPE AND A METHOD FOR EVALUATING ACCURACY OF REPEATED MEASUREMENT USING THE SAME

(75) Inventors: Ryo Nakagaki, Kawasaki (JP); Hiroki Kawada, Tsuchiura (JP); Chie Shishido, Yokohama (JP); Mayuka Oosaki, Yokohama (JP)

(73) Assignee: Hitachi High-Technologies Corporation, Tokyo (JP)

( * ) Notice: Subject to any disclaimer, the term of this patent is extended or adjusted under 35 U.S.C. 154(b) by 65 days.

(21) Appl. No.: 10/988,522

(22) Filed: Nov. 16, 2004

(65) Prior Publication Data
US 2005/0205780 A1 Sep. 22, 2005

(30) Foreign Application Priority Data
Mar. 16, 2004 (JP) ............................. 2004-073820

(51) Int. Cl.
*G01N 23/00* (2006.01)
(52) U.S. Cl. ...................... 250/311; 250/310; 250/306
(58) Field of Classification Search ..................... None
See application file for complete search history.

(56) References Cited
U.S. PATENT DOCUMENTS 5,887,080 A * 3/1999 Tsubusaki et al. .......... 382/172
6,111,981 A * 8/2000 Tsubusaki et al. .......... 382/172
6,774,364 B1 * 8/2004 Takagi ....................... 250/310

FOREIGN PATENT DOCUMENTS

JP 11-316115 11/1999

* cited by examiner

Primary Examiner—Nikita Wells
Assistant Examiner—Anthony Quash
(74) Attorney, Agent, or Firm—Antonelli, Terry, Stout and Kraus, LLP.

(57) ABSTRACT

The present invention relates to a CDSEM (scanning electron microscope) capable of evaluating and presenting the measurement repeatability as a tool with a high degree of accuracy without being influenced by fluctuations in microminute shape that tend to increase with the microminiaturization of semiconductor patterns, and to a method for evaluating accuracy of repeated measurement using the scanning electron microscope. There is provided a function whereby when measuring a plurality of times the same part to be measured, by making use of a micro-minute pattern shape such as the roughness included in the pattern, pattern matching with a roughness template image is performed to correct two-dimensional deviation in position of the part to be measured on an enlarged measurement image acquired, and then an enlarged measurement area image is extracted and acquired. This makes it possible to eliminate variation in measurements caused by the micro-minute pattern shape.

17 Claims, 7 Drawing Sheets

ADDRESSING IMAGE

MEASURED IMAGE (FIRST TIME)

MEASURED IMAGE (FIRST TIME)

MEASURED IMAGE (SECOND AND SUBSEQUENT MEASUREMENT)

MEASURED PATTERN

SCANNING ELECTRON MICROSCOPE AND A METHOD FOR EVALUATING ACCURACY OF REPEATED MEASUREMENT USING THE SAME

BACKGROUND OF THE INVENTION

The present invention relates to an electron microscope for performing CD measurement of semiconductor patterns having various kinds of shapes and dimensions, and more particularly to a scanning electron microscope having a function suitable for managing the measurement precision, and to a method for evaluating accuracy of repeated measurement using the scanning electron microscope.

In a semiconductor wafer manufacturing process, the microminiaturization of thin film patterns which are formed on a wafer in a multilayer structure rapidly progresses. Accordingly, the importance of process monitoring which monitors whether or not those patterns are formed on the wafer according to the design is more and more increasing. Above all, as far as transistor gate wiring and metal wiring made of aluminum, copper, or the like formed on a wafer, are concerned, there is a close relationship between the line width and device operation characteristics, and therefore manufacturing process monitoring of the line width is in particular important.

As a measurement tool for measuring the line width of the micro-minute wiring on the order of tens of nanometers, the scanning electron microscope (measurement SEM (Scanning Electron Microscope)), or the CD (Critical Dimension) SEM, which is used for measuring the line width and is capable of imaging the wiring with the magnification of from 100000 to 200000 times, is conventionally used. An example of measurement processing which uses such a scanning electron microscope is described in Japanese Patent Laid-Open No. Hei 11-316115. In the disclosed example of this document, from a local area in an image acquired by imaging a wiring line to be measured, image signal profiles of the wiring line are added and are averaged in the longitudinal direction of the wiring line to create a projection profile, and a wiring dimension is then calculated as a distance between right and left wiring edges detected in this profile. In addition, in the disclosed example of Japanese Patent Laid-Open No. Hei 11-316115, there is provided a function of displaying, on the same screen, the formed image, and the local area where the projection processing has been performed. Thereby, a user can check now easily about which wiring part was measured in the screen.

Incidentally, important indicators for evaluating measurement performance of CDSEMs include measurement repeatability. This measurement repeatability is expressed as the variation in measurements when measuring the same wiring a plurality of times. A smaller value of the variation means that the measurement performance is higher. Because semiconductor patterns to be measured are more and more microminiaturized, the measurement repeatability is more severely required for the CDSEMs.

Thus, it is considered that in future the requirements for the repeatability are severer and the amount of roughness tends to increase because a resist material which is sensitive to exposed illumination is used to create micro-minute patterns. Accordingly, it is expected that in future a measurement error caused by the influence of fluctuations in micro-minute shape cannot be ignored in association with a dimension error which a CDSEM might generate.

SUMMARY OF THE INVENTION

The present invention relates to a CDSEM (scanning electron microscope) capable of evaluating and presenting the measurement repeatability as a tool with a high degree of accuracy without being influenced by fluctuations in micro-minute shape that tend to increase with the microminiaturization of semiconductor patterns, and to a method for evaluating accuracy of repeated measurement using the scanning electron microscope.

To be more specific, according to one aspect of the present invention, there is provided a scanning electron microscope, the scanning electron microscope comprising: an image acquisition unit for scanning an electron beam on a sample under specified imaging conditions at each measurement over the number of times of measurement to acquire an enlarged measurement image at high magnification based on an electron signal emitted from the sample; an image processing unit for, from the enlarged measurement image at high magnification acquired at each measurement over the number of times of measurement by the image acquisition unit, acquiring a roughness template image showing a micro-minute shape of a pattern in a provided local area, and an enlarged measurement area image of the local area subjected to two-dimensional pattern matching; and a measurement unit for measuring dimensions or a shape of the pattern in the enlarged measurement area on the basis of the enlarged measurement area image of the local area, which has been acquired at each measurement over the number of times of measurement by the image processing unit.

In one embodiment of the invention, preferably, the image acquisition unit further includes a roughness template image acquisition unit for acquiring a roughness template image which is provided by the image processing unit, as the local area from the enlarged measurement image at high magnification acquired according to an electron signal emitted from a specified sample by scanning the electron beam on the specified sample.

In one embodiment of the invention, preferably, the image acquisition unit includes an addressing image acquisition unit for acquiring an addressing image having an addressing pattern formed on the sample; the image processing unit includes a coordinate acquisition unit for acquiring coordinates of the addressing pattern by pattern matching between the addressing image acquired by the addressing image acquisition unit and an addressing template image to thereby acquire coordinates of the enlarged measurement area from the acquired coordinates of the addressing pattern; and the image acquisition unit is configured to acquire the enlarged measurement image on the basis of the coordinates of the enlarged measurement area acquired by the coordinate acquisition unit.

Preferably, the scanning electron microscope according to the present invention further comprises: a measurement repeatability evaluation unit for presenting, as the evaluation value of the measurement repeatability as the tool, a value associated with the change in dimensions or the change in shape for the number of times of measurement, the dimensions or the shape being measured over the number of times of measurement by the measurement unit.

In one embodiment of the invention, preferably, the measurement repeatability evaluation unit uses variation in dimensions or variation in shape for the number of times of measurement as the presented value in response to the change in dimensions or the change in shape for the number of times of measurement.

In one embodiment of the invention, preferably, in response to the change in dimensions or the change in shape for the number of times of measurement, the dimensions or the shape being measured over the number of times of measurement, the measurement repeatability evaluation unit determines a function model with the best fitting by performing a fitting process for a plurality of function models, and then presents the determined function model as the evaluation value of the measurement repeatability as the tool.

In one embodiment of the invention, preferably, in response to the change in dimensions or the change in shape for the number of times of measurement, the dimensions or the shape being measured over the number of times of measurement, the measurement repeatability evaluation unit determines a function model with the best fitting by performing a fitting process for a plurality of function models, and then calculates the deviation of the change in dimensions, or that of the change in shape, for the number of times of measurement, from the determined function model to present a value in response to the calculated deviation as the evaluation value of the measurement repeatability as the tool.

In one embodiment of the invention, preferably, in response to the change in dimensions or the change in shape for the number of times of measurement, the dimensions or the shape being measured over the number of times of measurement, the measurement repeatability evaluation unit determines a function model with the best fitting by performing a fitting process for a plurality of function models, and then calculates the deviation of the change in dimensions, or that of the change in shape, for the number of times of measurement, from the determined function model to present variation in the calculated deviation as the evaluation value of the measurement repeatability as the tool.

In one embodiment of the invention, preferably, the measurement repeatability evaluation unit also presents the imaging conditions used in the image acquisition unit as the evaluation value of the measurement repeatability as the tool.

According to the present invention, it is possible to eliminate a measurement error caused by the change in micro-minute shape such as the line edge roughness included in a wiring pattern, and to present the measurement repeatability as a tool with a high degree of accuracy of about 1 to 2 nm or less without being influenced by a target to be measured.

Furthermore, according to the present invention, it is possible to effectively eliminates the influence of the contamination appearing when measuring the same sample a plurality of times, and to evaluate the measurement repeatability as the tool with a high degree of accuracy of about 1 to 2 nm or less.

These and other objects, features and advantages of the invention will be apparent from the following more particular description of preferred embodiments of the invention, as illustrated in the accompanying drawings.

BRIEF DESCRIPTION OF THE DRAWINGS

FIG. 3A illustrates an addressing image; FIGS. 3B and 3C are diagrams each illustrating a measured image acquired at the first measurement; and FIG. 3D illustrates a measured image acquired at the second measurement or later;

DESCRIPTION OF THE PREFERRED EMBODIMENTS

Embodiments of a CDSEM (scanning electron microscope) according to the present invention will be described with reference to drawings.

Because semiconductor patterns to be measured are more and more microminiaturized, the measurement repeatability is more severely required for a CDSEM according to the present invention. In manufacturing monitoring of current semiconductor pattern formation process, if a formation error of a pattern itself is also taken into consideration, an error allowable for the pattern measurement is said to be about 2% of a pattern size (dimension). Therefore, it is expected that the measurement repeatability required in the near future will be about 0.5 [nm].

Figure 4:
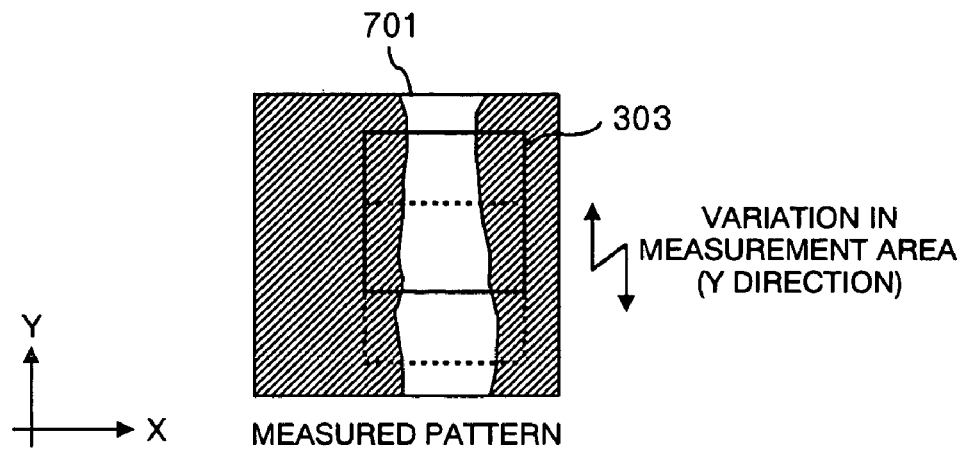
FIG. 4 is a diagram illustrating the line edge roughness.

Incidentally, in parallel with the measurement repeatability that is more severely required as a result of the microminiaturization of patterns, a change in micro-minute shape of a pattern caused by the microminiaturization of patterns comes to exert an influence upon evaluation of the repeatability. This change in micro-minute shape means fluctuations in micro-minute shape such as line edge roughness occurring at the edges of a wiring pattern 701 as shown in FIG. 4.

In the present invention, therefore a resist material which is sensitive to exposed illumination is used to make microminute patterns. Accordingly, even if the amount of roughness tends to increase, as shown in FIG. 4, always measuring the same part a plurality of times with a measurement area 303 not varying relative to the Y direction at each measurement makes it possible to properly evaluate the measurement repeatability.

Figure 1:
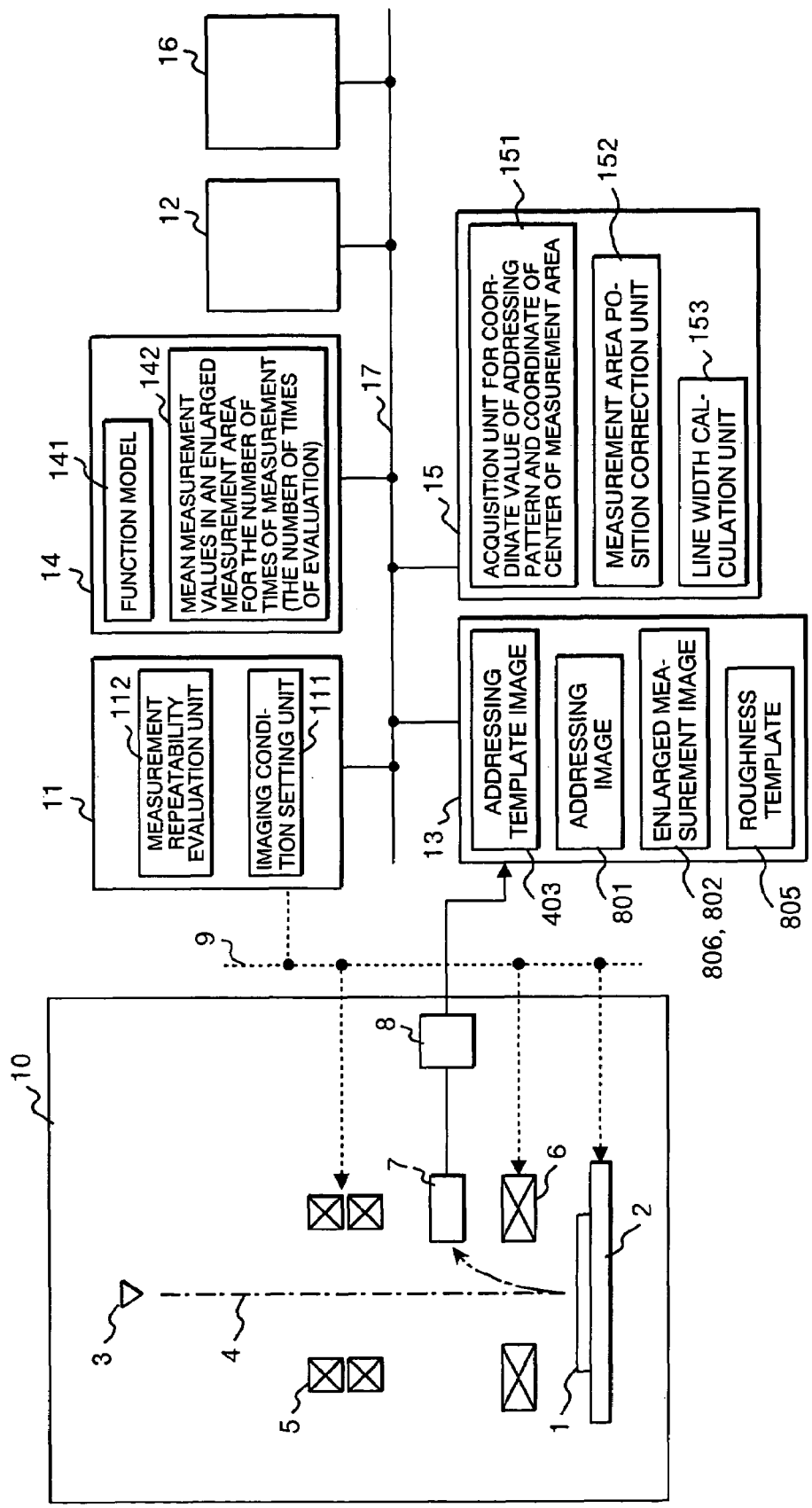
FIG. 1 is a diagram schematically illustrating a functional configuration of a scanning electron microscope according to one embodiment of the present invention.

FIG. 1 is a schematic diagram illustrating how a CDSEM according to one embodiment of the present invention is configured. Broadly classifying, the CDSEM comprises: an electro-optical system 10 used for imaging; a total control unit 11 that controls the imaging of an image, move of a stage, and the like, and that sets imaging conditions, said total control unit 11 having a control CPU used to evaluate the measurement repeatability; an input/output unit 12 through which a user inputs data, and through which an acquired image is displayed; an image storage unit 13 for storing data required for the CDSEM, for example, image data including an addressing template image 403, an addressing image 801 that has been imaged, enlarged measurement images 802, 806, each measurement area of which is imaged in an enlarged form, and a roughness template 805; a main storage unit 14 that stores a program for operating the CDSEM and function models, and that stores measurement values at a plurality of points in an enlarged measurement area for the number of times of measurement (the number of times of evaluation), said measurements being calculated by a line width calculation unit 153 of a processing unit 15; a processing unit 15 having a CPU, said processing unit 15 performing various kinds of image processing to present the result on a display unit 16, or the like, through the total control unit 11; and the display unit 16.

The total control unit 11 includes an imaging condition setting unit 111 for setting imaging conditions (an acceleration voltage of an incident beam, a beam current, the imaging magnification, the amount of beam irradiation (the dose amount) to an observation area, and the like). Set values of the imaging conditions are presented on the display unit 16, or the like. As another function, the total control unit 11 further includes a measurement repeatability evaluation unit 112 for evaluating the measurement repeatability on the basis of the measurement values at the plurality of points in the enlarged measurement area for the number of times of measurement (the number of times of evaluation), said measurement values being stored in the main storage unit 14. The processing unit 15 may also be functionally provided with this measurement repeatability evaluation unit 112. The processing unit 15 functionally includes: a coordinate acquisition unit 151 for acquiring coordinate values of an addressing pattern and coordinates of the center of a measurement area; a measurement area position correction unit 152; and a line width calculation unit 153.

The total control unit 11, the input/output unit 12, the image storage unit 13, the main storage unit 14, the processing unit 15, and the display unit 16 are connected to one another through a data bus 17 so that required data can be transmitted. In addition, the electro-optical system 10 is configured to include an electron gun 3, a deflector 5, an objective lens 6, a secondary electron detector 7, an analog-to-digital converter 8, and a stage 2 on which a sample is placed. Each part of the electro-optical system is connected to the total control unit 11 through a control bus 9, and performs various kinds of operation (move of the stage, electron beam deflection, focusing controlled by an objective lens, and the like) according to an instruction from the total control unit 11.

An operation sequence of this CDSEM will be described as below. To begin with, a sample to be observed 1 is placed on a stage 2. Next, as soon as a user specifies position information about a part to be observed, the total control unit 11 gives an instruction to the stage 2 through a control bus 9, and thereby positioning of the stage is carried out so that the part comes into an observed visual field. Next, when an electron beam 4 is emitted from an electron gun 3, a path of the electron beam 4 is deflected by the deflector 5, and is then converged by the objective lens 6. As a result, the sample 1 is irradiated with the electron beam 4. The secondary electron detector 7 detects a secondary electron emitted from the sample 1, and then converts the intensity thereof into an electric signal. An analog-to-digital converter 8 converts the converted electric signal into a digital signal (a gray scale signal of the intensity of the secondary electron). In this CDSEM, it is possible to acquire a two-dimensional SEM image by controlling the deflector 5 so that an area of the sample scanned with the electron beam 4 becomes rectangular, and by inputting digital signal data in synchronization with the scanning. This image data is stored in an image data storing part included in the image storage unit 13.

Figure 2:
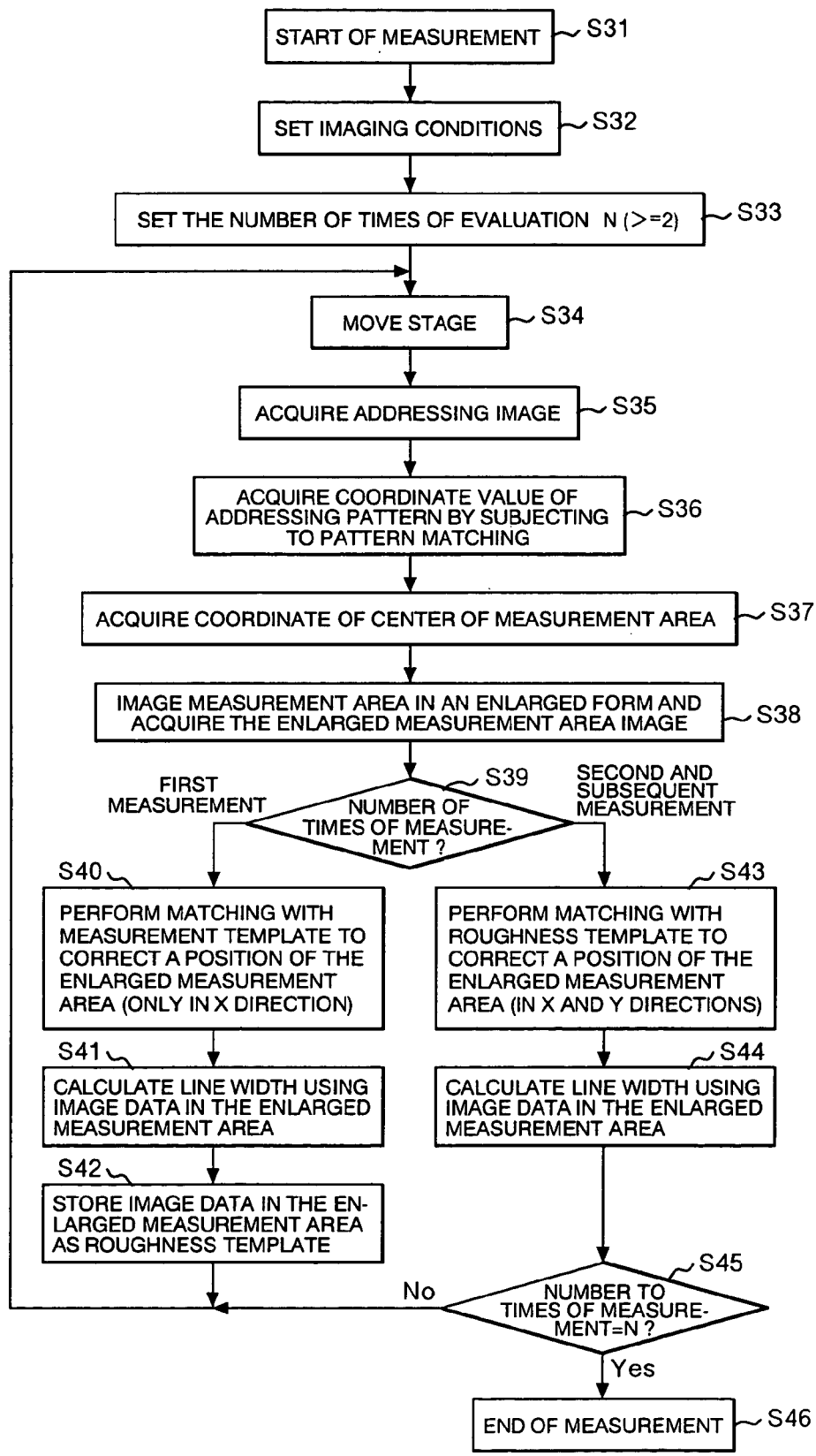
FIG. 2 is a flowchart illustrating a first embodiment of a sequence of measuring the line width (CD) of a pattern in the same measured part a plurality of times by use of a scanning electron microscope according to the present invention.
Figure 6:
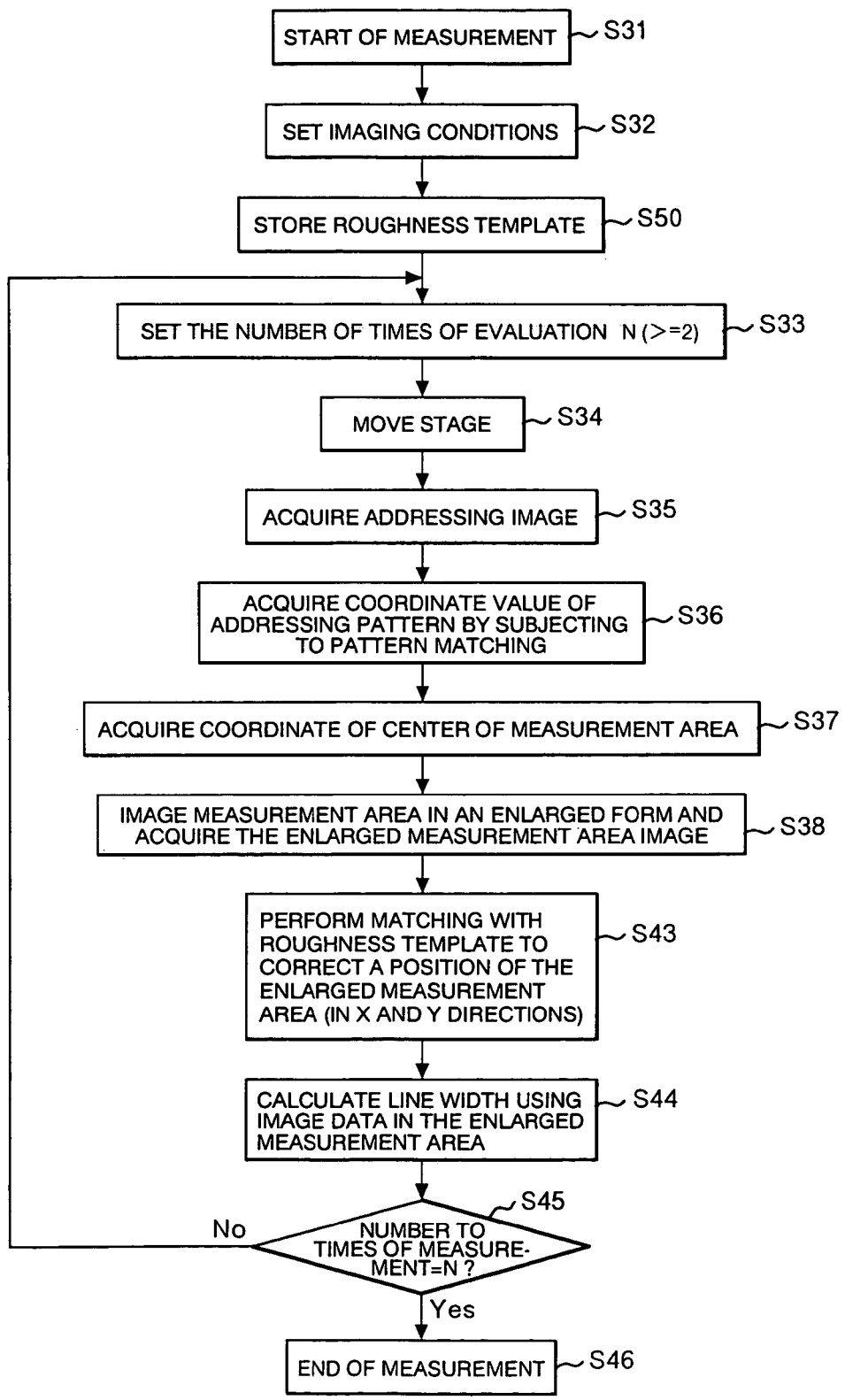
FIG. 6 is a flowchart illustrating a second embodiment of a sequence of measuring the line width (CD) of a pattern in the same measured part a plurality of times by use of a scanning electron microscope according to the present invention.
Figure 7:
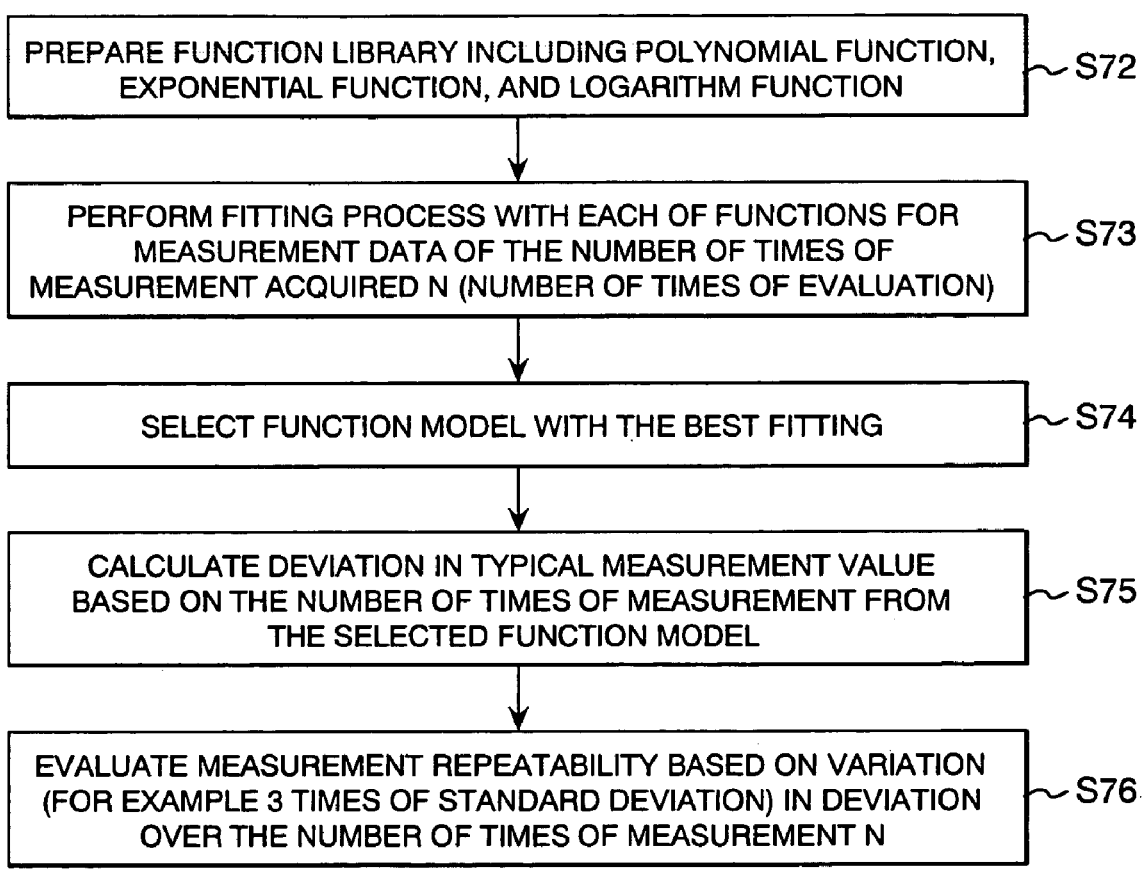
FIG. 7 is a flowchart illustrating one embodiment of the measurement repeatability evaluation sequence of a scanning electron microscope according to the present invention.

The total control unit 11 controls the processing unit 15, and the like, so that processing shown in FIG. 2 or FIGS. 6 and 7 is executed. In addition, the total control unit 11 calculates evaluation values (in particular, 3s value of variation) of the measurement repeatability shown in FIGS. 8A and 8B associated with imaging conditions, and then presents the evaluation values on the display unit 16, or the like.

Control of each part required to actually image an image (for example, imaging magnification control, and imaging position control) is also performed by giving an instruction from the total control unit 11 to each part through the control bus 9 in a similar manner. For example, the magnification control can be achieved by controlling the deflector 5. To be more specific, making the rectangular area to be two-dimensionally scanned with an electron beam wide enables low magnification imaging, whereas making the rectangular area to be two-dimensionally scanned narrow enables high magnification imaging. Further, controlling the deflector also makes it possible to move a position to which an electron beam is applied (more specifically, an image acquisition position) in an imaging visual field.

In an image processing unit 15, as a result of image processing, such as image matching, which is performed in the sequence shown in FIG. 2 or 7, the coordinate acquisition unit 151 acquires coordinate values of an addressing pattern and coordinates of the center of a measurement area; the measurement area position correction unit 152 corrects a position of the measurement area (two-dimensional position in X, Y directions) by matching with a roughness template; and the line width calculation unit (measurement unit) 152 calculates line width measurement values. The measurement repeatability evaluation unit 112 in the total control unit 11 evaluates the measurement repeatability shown in FIGS. 8A and 8B according to processing shown in FIG. 7.

In addition, the sequence of operation can be automatically carried out by storing in the main storage unit 14 a program that describes the sequence of imaging operation (move of the stage, imaging of an image, acquisition of coordinates, correction of a position of a measurement area, calculation of line width measurement values, evaluation of the measurement repeatability, and the like), and by instructing the total control unit 11 to execute the sequence if necessary.

Figure 5:
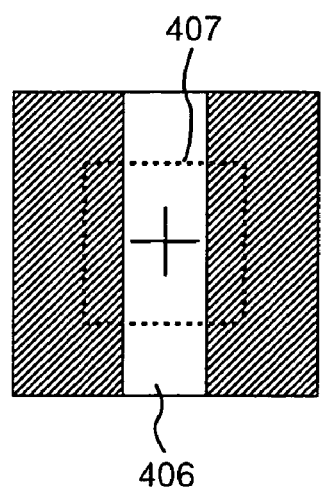
FIG. 5 is a diagram illustrating how to correct the deviation of visual field in the X direction in a part to be measured.

Next, a first embodiment of a sequence of measuring a plurality of times the line width (CD) of a pattern in the same measured part (typical dimensions or shape of the pattern (measurement values at a plurality of points)) using a CDSEM according to the present invention will be described with reference to FIG. 2 or 5.

In the first place, the total control unit 11 starts measurement (S31). Next, the imaging condition setting unit 111 of the total control unit 11 sets imaging conditions of the electro-optical system 10 in the CDSEM (an acceleration voltage of an electron beam, a beam current, the imaging magnification, the amount of dose, and the like) (S32). Then, a user uses an input means 12 to specify the number of times of measurement (the number of times of evaluation) N for the total control unit 11 (S33). Main imaging conditions which should be set for the imaging of an image by a SEM include: an acceleration voltage of an incident beam; a beam current; the imaging magnification; and the amount of beam irradiation (dose amount) to an observation area. The above information is stored in a file, or the like, in the main storage unit 14. The information is reads out at the time of observation. However, a user may also set the information for the total control unit 11 by manual operation using the input unit 12.

Next, through processing as describe below, a part to be measured, which is determined in advance, is measured N times under the set imaging conditions described above to acquire measurement values of the line width (typical dimensions or shape) of a pattern.

The measurement, the number of times of which is N, means in a broad sense that with respect to a certain sample, while giving an instruction to keep conditions including an acceleration voltage the same, the sample to be imaged (for example, a semiconductor wafer) is measured a plurality of times. In the measurement, the number of times of which is N, there is, for example, a case where a sample is first put in a cassette (not illustrated) provided outside the SEM, and what is repeatedly performed N times is a sequence of: loading the sample from the cassette to a vacuum chamber of the SEM; measuring the sample; and unloading the sample to the cassette. There is also a case where after loading a wafer to a vacuum chamber, what is alternately repeated N times before unloading the wafer to the wafer cassette is: measurement processing of the target to be measured; and move of a stage or a beam scan range, which is performed so that the target to be measured comes into an imaging visual field. Moreover, there is also a case where after loading a wafer, a part to be measured is positioned in a visual field, and then the wafer is measured N times in succession before unloading the wafer. As a matter of course, it is not necessary to load and unload a wafer before and after measurement. The wafer may also be placed on the stage before measurement, and the wafer may also be left on the stage after measurement.

Figure 3A:
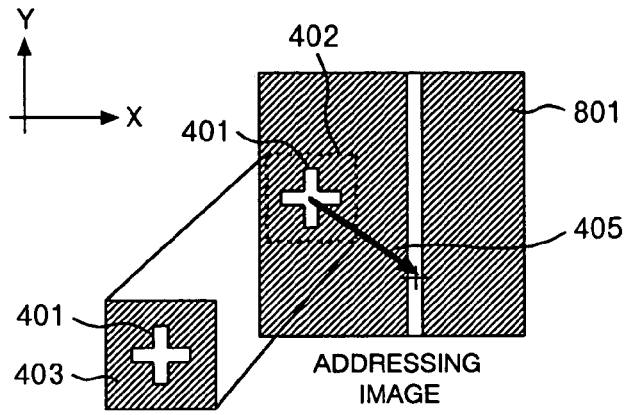
FIGS. 3A to 3D are diagrams each illustrating an image acquired in a measurement sequence according to the present invention.

The measurement processing at each measurement point will be described as below. To begin with, position information about a target to be measured is read out from the storage unit 13 or is acquired from the input unit 12. Then, the stage of the CDSEM is moved according to an instruction from the total control unit 11 so that a part of the target comes into an imaging visual field (S34). After that, the part is imaged under the set imaging conditions described above to acquire an addressing image 801 shown in FIG. 3A (S35). The addressing image 801 is then stored in the image storage unit 13. This addressing image 801 is an image, a visual field of which includes a part to be measured, and an addressing pattern 401 existing around the part to be measured. The addressing image 801 is imaged at magnification of about tens of thousands of times. Next, the coordinate acquisition unit 151 of the image processing unit 15 performs pattern matching processing which targeted the acquired addressing image 801 by making an addressing template image 403 into a template. Here, the addressing template image 403 is an image of the addressing pattern 401 inside the addressing image 402, which is stored beforehand in the storage unit 13. As a result of the pattern matching processing, the coordinate acquisition unit 151 acquires a position (coordinate values) of the addressing pattern 401 in the acquisition addressing image 801 (S36). In this pattern matching processing, image matching algorithm such as the cross correlation method is used. Incidentally, the addressing template image 403 can be imaged by use of, for example, a wafer for recipe creation, and can be stored in the image storage unit 13.

Figure 3B:
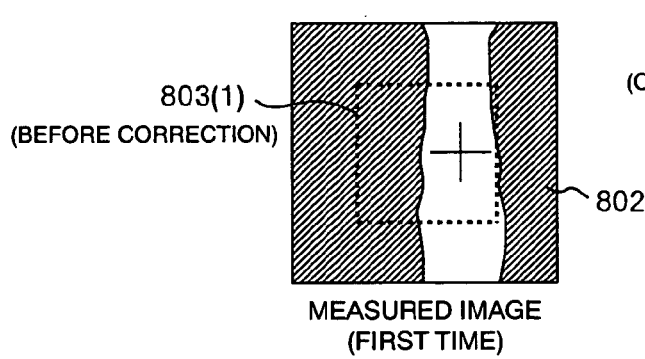
Figure 3C:
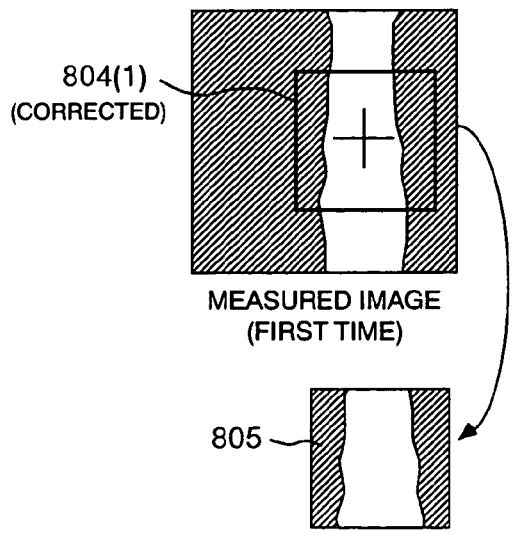

Next, the coordinate acquisition unit 151 of the image processing unit 15 acquires coordinates of the center of the measurement area in the addressing image 801 from relative distance information 405 between the addressing pattern 401 and the measurement position 404 (S37) and transmits the acquired coordinate information to the total control unit 11. The addressing pattern 401 can be acquired by imaging an addressing pattern on the wafer in the SEM, which is created beforehand by the same design pattern, or can be obtained by storing in the image storage unit 13 through the input unit 12 from a CAD system (not illustrated), or the like. Then, the stage 2 and the electro-optical system 10 are controlled according to instructions from the total control unit 11 so that an applying position of an electron beam is relatively moved to the center of the measurement area before scanning the electron beam. As a result, as shown in FIG. 3B, an enlarged image (enlarged measurement image 802) at a specified measurement position is acquired (S38), and the enlarged image is then stored in the image storage unit 13. Because it is necessary to perform the imaging with the line width (dimensions or a shape) of a pattern being enlarged, this measured image is usually acquired at magnification of about hundreds of thousands of times. Thus, the reason why images having two kinds of magnification are used is because if an image of high magnification is acquired at a time, a problem of the positioning accuracy of the stage 2 causes a possibility that a target pattern will not come into a visual field.

Here, the total control unit 11 identifies what number of times of measurement an image currently being acquired corresponds to (S39). If it is the first measurement, the measurement area position correction unit 152 of the image processing unit 15 is instructed to correct deviation in visual field in the X direction by pattern matching so as to eliminate a positioning error of an electron beam only in the X direction as described below (S40). The positioning error of an electron beam is a phenomenon in which even if the imaging of an image is performed after an electron beam is positioned so that a certain point in a wafer comes into the center of a visual field, this point deviates from the center of an actually acquired image. In response to for example an electrification state of an electric charge on a wafer surface, a path of an electron beam changes on the surface of the sample. The above deviation in position is thought to be caused by the change in the path. The amount of the positioning error of an electron beam changes according to various conditions including the quality of material of the target. However, it is confirmed that the amount of the positioning error is roughly about few tens of nm. As shown in FIG. 5, information stored for the pattern matching processing performed to correct the deviation in visual field includes: an enlarged measurement template image 406 of a wiring pattern stored beforehand; and an enlarged measurement area 407 showing a line width part to be measured in the enlarged template image. The stored information is used to make corrections of: the deviation in visual field of an acquired image (if the wiring pattern has been read out from the visual field); and the deviation in X direction position of the line width part to be measured.

To be more specific, as for the enlarged measurement image 802 acquired as a result of imaging in an enlarged form, a wiring part to be measured deviates from the center of the visual field due to the positioning error of the electron beam. At this point of time, as shown in FIG. 5, because a relative position of an enlarged measurement area 803 (1) relative to an image frame is the same as that of the stored measurement area 407, the positional relation of the enlarged measurement area 803 (1) with an image of the wiring pattern imaged in an enlarged form is not proper. For this reason, the measurement area position correction unit 152 of the image processing unit 15 calculates, by the pattern matching method, the amount of the deviation in X direction position between this enlarged measurement image 803 (1) and the enlarged measurement template image 406. General image matching algorithm such as the cross correlation method can be used also in this processing.

Next, the measurement area position correction unit 152 of the image processing unit 15 shifts in the X direction the enlarged measurement area 803 (1) in the enlarged measurement image 802 (shifts in the X direction a line width measurement part on a measured image) only by the calculated amount of deviation in X direction position, and thereby determines a measurement target area 804 (1) after the correction (S40). The line width calculation unit (measurement unit) 153 of the image processing unit 15 calculates measurement values at a plurality of points showing typical dimensions (for example, a mean value of CD) or a shape by use of the image data in the area 804 (1), and then stores the measurement values as measurement values 142 of the main storage unit 14 (S41).

The measurement value of the line width are calculated first by determining right and left edges of a signal profile (a gray scale signal of the intensity of the secondary electron) 805 of the wiring pattern acquired from the enlarged measurement area 804 (1) on the basis of some reference point (for example, a point at which a tilt of the profile (gray value) becomes the maximum value is treated as an edge), and by determining as typical dimensions a mean value of a large number of distances between the edges where fluctuations in micro-minute shape such as line edge roughness have occurred, and then by adopting the mean value as the measurement of the line width. Incidentally, the profile 805 in the figure shows a typical shape of the profile (a change in micro-minute shape of a pattern caused by the microminiaturization of patterns), which is acquired when imaging a line pattern in an enlarged form by the CDSEM. This change in micro-minute shape means fluctuations in micro-minute shape such as line edge roughness occurring at the edges of a wiring pattern.

In the meantime, although an isolated wiring pattern (a long wiring pattern around which no other wiring exists) is taken as an example of a wiring pattern, it is possible to acquire an enlarged image and to calculate measurements in a similar sequence also in the case of a line and space pattern (a pattern in which lines are densely arranged at equal intervals) or a hole pattern.

Next, according to an instruction from the total control unit 11, the image processing unit 15 stores the enlarged image pattern of the enlarged measurement area 804 after the correction, which has been determined by the first measurement sequence, in the image storage unit 13 as a roughness template 805 (S42). This roughness template 805 is used at the second measurement or later. It is to be noted that the roughness template 305 is not necessarily be enlarged image data itself of the enlarged measurement area 804 after the correction. If there is characteristic roughness of a shape occurring around the area, enlarged image data of the area may also be used as the roughness template 305.

In addition, as a result of calculating the deviation in visual field of the enlarged measurement area 803 (1) by the image processing unit 15 according to the first measurement sequence, if the amount of the deviation in visual field is not too large to include the wiring to be measured in the enlarged measurement area, it is not always necessary to correct the enlarged measurement area. In this case, the measurement is performed by use of enlarged image information in the enlarged measurement area 803 (1) before the correction, and the result of the measurement may also be stored as a roughness template 805.

The first sequence described above is basically a sequence of acquiring the roughness template 805 and then storing it in the image storage unit 13 in the image processing unit 15.

Figure 3D:
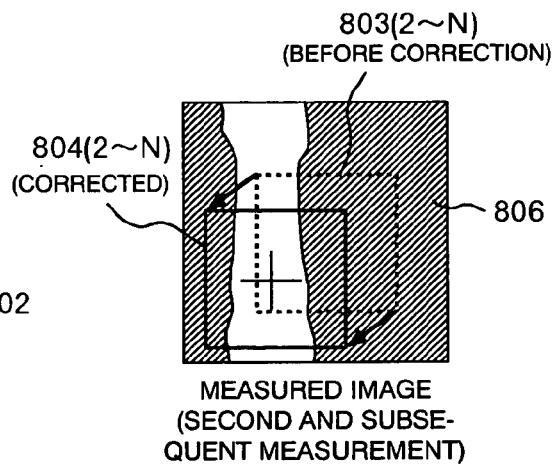

A characteristic point of the present invention is that the second measurement or later is performed using the acquired roughness template 805. To be more specific, in a step S42, enlarged image data in the enlarged measurement area is stored in the image storage unit 13 as the roughness template 805, and then steps S34 through S38 are executed according to instructions from the total control unit 11. As a result, as shown in FIG. 3D, the enlarged measurement image 806 of the second measurement or later is acquired, and then the acquired enlarged measurement image 806 is stored in the image storage unit 13. At this time, the total control unit 11 judges the number of times of measurement to be two or more in a step S39, and consequently the process proceeds to a step S43. In this case, the measurement area position correction unit 152 of the image processing unit 15 performs image matching with the stored roughness template 805 being used as a template, and with the acquired enlarged measurement image 806 being used as a target. Then, the measurement area position correction unit 152 calculates positions 804 (2 through N) in the X and Y directions at which the roughness pattern template 805 exists in the enlarged measurement image 806, and corrects the positions in the X and Y directions (2 dimensions) in the enlarged measurement area. As a result, an image to be measured in the enlarged measurement area is extracted and acquired (S43). In this case, it is possible to present the amount of deviation in position of reference numeral 803 (2 through N) relative to reference numeral 804 (2 through N), and position coordinates of the reference numeral 804 (2 through N), on the display unit 16.

Here, because the roughness template 805 is used, it is possible to detect positions of the enlarged measurement area 804 (2 through N) in both the X and Y directions with a high degree of accuracy. Moreover, correcting them makes it possible to acquire an image to be measured in the enlarged measurement area. It is to be noted that the reference numeral 803 (2 through N) denotes an enlarged measurement area before correction at coordinates of the center of the enlarged measurement area acquired in the step S37. The reference numeral 804 (2 through N) denotes an enlarged measurement area after the correction, the position of which has been detected. Thus, the image matching (pattern matching) is performed by use of the roughness template 805 for the second measurement or later so that patterns agree with each other in both the X and Y directions with a high degree of accuracy. Accordingly, for example, even if fluctuations in micro-minute shape occur in a micro-minute wiring pattern having the size of about 100 nm or less, as shown in FIG. 4, it is possible to prevent the enlarged measurement area from deviating in the Y direction as a result of performing the measurement a plurality of times.

Next, the line width calculation unit 153 of the image processing unit 15 calculates, for example, a mean value of a large number of line width measurement values between edges by use of enlarged image data (enlarged image data of the same measured part) in the corrected enlarged measurement area 804 (2 through N), and then stores the mean value as the measurement value 142 of the main storage unit 14 (S44).

As describe above, from the second measurement, it is possible to acquire measurement values, the total number of times of which is N, and to store them in the main storage unit 14, by repeating the steps S34 through S44 (S45) the number of times of measurement (the number of times of evaluation) inputted in the step S33. Here, each of the measurement values is, for example, a mean measurement value which represents between a large number of edges in the enlarged measurement area 804. All of the measurement values acquired by this sequence are based on the same point on the pattern, and therefore do not include dispersion of values caused by the deviation in visual field. Incidentally, in this embodiment, the roughness template 805 itself acquired by the first measurement is used for the pattern matching in the second measurement or later. However, the method is not limited to this. An image (for example, a roughness template image which emphasized image edge information which can acquire by applying an edge filter to a roughness template) as a result of performing the image processing for the roughness template image 805 can also be used. Incidentally, in this case, the image matching is carried out after performing similar image processing also for the enlarged measurement image 806 that is a target of the pattern matching.

In the first embodiment described above, among N, which is the number of times of measurement set by the user, the roughness template 805 in the first measurement is stored, and the stored data is used for the second measurement or later. However, it is not always necessary to acquire the roughness template 805 from the first enlarged image data. For example, another method includes steps of: selecting an arbitrary enlarged image after acquiring M pieces of enlarged images; acquiring a roughness template from the selected enlarged image; correcting the deviation of the enlarged measurement area in other enlarged image data with respect to the X and Y directions by use of the acquired roughness template; and calculating measurement values in the corrected enlarged measurement area. A surface state of an electron-beam image is thought to change as a result of the contamination adhering to a sample at each measurement. Therefore, if the number of times of measurement is many, it is expected that the appearance of roughness in an enlarged measurement image at the first measurement will differ from that at the Nth measurement. In this case, the roughness template 805 can be created from an imaged image selected from (for example, the N/2 th) among N pieces of images. In another case, among measurements acquired from the first to the Nth measurement, the roughness template 805 is stored at predetermined intervals (for example, every three times), and the roughness template 805 is updated with the increase in the number of times of measurement.

Next, a second embodiment of a sequence of measuring a plurality of times the line width (CD) of a pattern in the same part (typical dimensions or shape of the pattern) using a CDSEM according to the present invention will be described with reference to FIG. 6. In the first embodiment described above, among N, which is the number of times of measurement (the number of times of evaluation) set by a user, the roughness template 805 is stored at the first measurement; and at the second measurement or later, a measurement area is align using this roughness template 805. However, in the second embodiment, the timing of storing the roughness template 805 is not always limited to the first measurement among N, which is the number of times of measurement. For example, as shown in FIG. 6, the following method may also be adopted: prior to data measurement, the number of times of measurement is N, performed in the steps S33 through S38, and S43 through S45, imaging in advance a part to be measured in a step S50; and extracting the roughness template 805 from the imaged image to store the roughness template 805 in the storage unit 13.

FIG. 6 illustrates a process flow of the second embodiment. To begin with, the imaging condition setting unit 111 of the total control unit 11 sets imaging conditions (an acceleration voltage of an electron beam, a beam current, the imaging magnification, the amount of dose, and the like) for the CDSEM (S32). Next, an enlarged measurement image at a measurement point is acquired. After that, the roughness template 805 is extracted from the enlarged measurement image, and is then stored in the storage unit 13 (S50). In this processing, the acquisition of the enlarged image by moving the stage 2, the extraction of the roughness template 805 from the acquired enlarged image, and storing of the roughness template 805, may also be performed by manual operation, or may also be automatically performed using the imaging sequence shown in FIG. 2. Next, N, which is the number of times of measurement, is specified for the total control unit 11 by a user (S33). Then, under the imaging conditions set for the same measured part that is predetermined, measurement is performed N times to acquire, for example, a mean measurement value (mean CD value) corresponding to typical dimensions of a pattern in the enlarged measurement area 804 at each measurement, and then to store the mean measurement value for each time in the reference numeral 142 of the main storage unit 14 (S34 through S38, and S43 through S45).

Incidentally, measurements in the enlarged measurement area 804 are acquired at each measurement in a manner similar to that of the first embodiment.

What will be described next with reference to FIGS. 7 and 8 is an embodiment of a sequence of evaluating the measurement repeatability of a CDSEM on the basis of measurement values acquired by performing measurement a plurality of times according to the sequence in the first and second embodiments of the present invention. As described above, when evaluating the measurement repeatability of the subnano order, there is a possibility that it will not be possible to model, in a straight line, thickening of a pattern caused by the contamination of an electron beam.

Figure 8A:
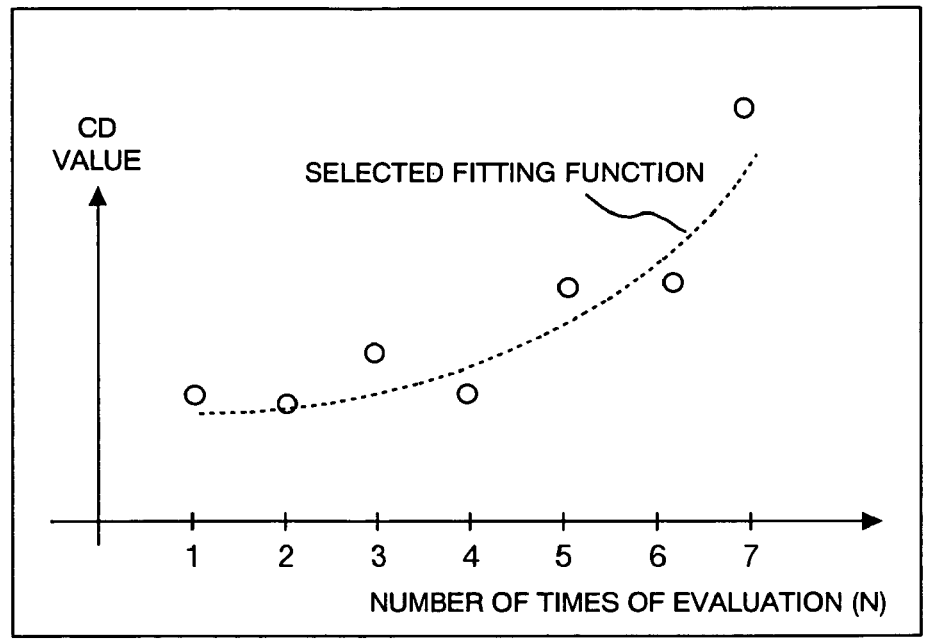
FIG. 8A is a graph illustrating a case where it is not possible to model, in a straight line, thickening of a pattern caused by the contamination of an electron beam.
Figure 8B:
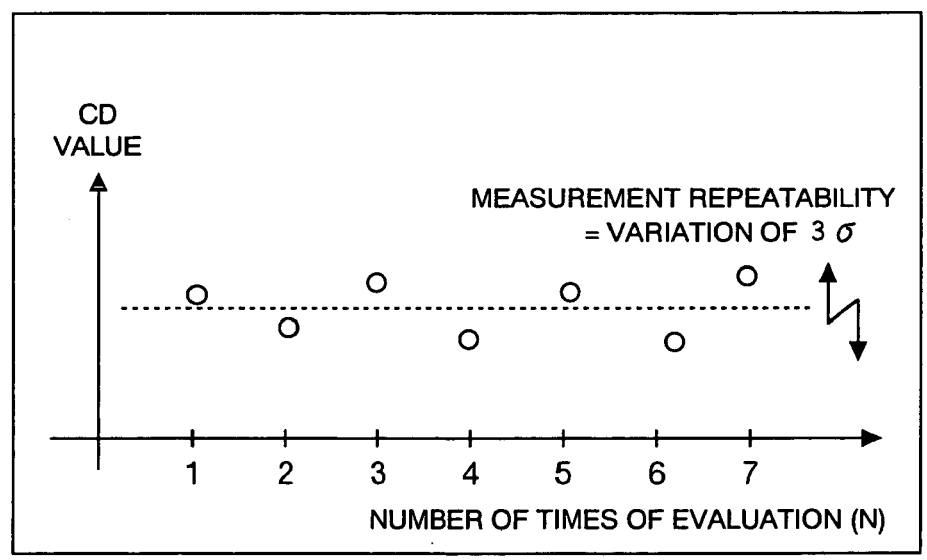
FIG. 8B is a graph illustrating an example in which each measurement, the increase in CD value of which has been corrected by a function model, is plotted with the horizontal axis being the number of times of measurement, and with the vertical axis being a CD value.

FIG. 8A is a graph schematically illustrating such an example. This figure illustrates a state in which with the increase in the number of times of measurement (the number of times of evaluation), a typical CD value (mean CD) of a pattern in each enlarged measurement area 804 parabolically increases. It is not desirable to apply a straight line to such data so that the repeatability is evaluated from the deviation in value from the straight line. For this reason, according to the present invention, as shown in a flowchart in FIG. 7, several function models 141 are stored beforehand, for example, in the main storage unit 14 of a CDSEM (S72). Then, in the measurement repeatability evaluation unit 112 of the total control unit 11, with each of the function models, a fitting process of measurement data acquired as a result of performing measurement a plurality of times (1 through N) is performed (S73) to select from among those function models a function model that best fits a tendency of the change in typical CD value (S74). Next, for each measurement (1 through N), a value of the deviation (ΔW (i)= (Wmean (i)−Ws (i))) in typical CD value (Wmean (i)=Wmean (1) through Wmean (N)) from a value of the function model (Ws (i)=Ws (1) through Ws (N)) is calculated (S75). After that, as shown in FIG. 8B, the measurement repeatability is evaluated based on amount of variation (for example, 3 times of standard deviation) in the values of the calculated deviations over the number of times of measurement (S76), and the result is presented, for example, on the display unit 16. In this case, as shown in FIG. 8A, what are displayed on the display unit 16 may include: a typical measurement value of the pattern acquired from the same measured part at each measurement over the number of times of measurement; the function model that best fits the change in typical measurement value of the pattern over the number of times of measurement; and the imaging conditions that are image acquisition conditions. Further, the display unit 16 may also present the roughness template image 805, and the enlarged measurement area images 804 (1 through N) that are acquired by measuring the same measured part over the number of times of measurement.

To be more specific, the above is achieved by steps of: (1) providing beforehand the CDSEM with a function library 141 including, for example, a polynomial function, an exponential function, and a logarithmic function (S72); and (2) as soon as measurement data (a typical CD value in the enlarged measurement area 804) is inputted a plurality of times, performing by the measurement repeatability evaluation unit 112 a least-squares fitting process for each of the function models in succession (S73). Here, an extent to which the measurement data fits the model is calculated on a model basis. As an indicator that expresses the extent of the fitting, for example, the sum of squares of the difference between a measured value (raw data) and model data (data corresponding to the data on a fitting curve) can be used. In this case, a smaller value means better fitting. The processing performed by the measurement repeatability evaluation unit 112 further comprises steps of: (3) selecting a function model with the best fitting (an expected value for the number of times of evaluation) (S74); (4) calculating the deviation of typical CD value in the enlarged measurement area 804 from the model (S75); and (5) evaluating the measurement repeatability based on value of amount of variation (for example, 3 times of standard deviation s) in deviation over the number of times of evaluation (S76). FIG. 8B is a graph illustrating an example in which each measurement, the increase in CD value of which has been corrected by a function model, is plotted with the horizontal axis being the number of times of measurement, and with the vertical axis being a CD value. Incidentally, as for the selection of this function model, as described here, it is also possible to automatically select an optimum function model using some criteria, and it is also possible to use a function model that is specified by a user by manual operation.

As described in the first and second embodiments, the CDSEM has the measurement sequence and a function of calculating the measurement repeatability from a plurality of measurements. If the CDSEM is provided with a user interface for displaying the progress and its result data on the display unit 16, a user can visually grasp an operation state of the processing and the measurement repeatability. For example, the user can easily check the operation and a phenomenon as a result of presenting to the user, through the input/output unit 12 or the display unit 16, information including: various kinds of image data, information about the enlarged measurement area, and the like, which are shows in FIGS. 3 through 5; the tendency of increase in CD value that can be read from a plurality of measurements shown in FIGS. 8A and 8B; a function model that is calculated from them; and measurement data, the increase in CD value of which has been corrected by the model.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description and all changes which come within the meaning and range of equivalency of the claims are therefore intended to be embraced therein.

What is claimed is:

1. A scanning electron microscope comprising:
   an image acquisition unit which scans an electron beam on a sample under specified imaging conditions at each measurement over the number of times of measurement to acquire an enlarged measurement image at high magnification based on an electron signal emitted from the sample;
   an image processing unit which acquires an enlarged measurement area image of a local area by using two-dimensional pattern matching with a roughness template image showing a micro-minute shape of a pattern in the local area, from the enlarged measurement image at high magnification acquired at each measurement over the number of times of measurement by the image acquisition unit;
   a measurement unit which measures typical dimensions or a shape of the pattern in the enlarged measurement area on the basis of the enlarged measurement area image of the local area, which has been acquired at each measurement over the number of times of measurement by the image processing unit; and
   a measurement repeatability evaluation unit which presents, as an evaluation value of the measurement repeatability as a tool, a value associated with the change in dimensions or the change in shape for the number of times of measurement, said dimensions or said shape being measured over the number of times of measurement by the measurement unit.

2. A scanning electron microscope according to claim 1, wherein:
   said image acquisition unit further includes a roughness template image acquisition unit which acquires the roughness template image provided by the image processing unit, as the local area from an enlarged measurement image at high magnification acquired according to an electron signal emitted from a specified sample by scanning the electron beam on the specified sample.

3. A scanning electron microscope according to claim 1, wherein:
   said image acquisition unit is further configured to acquire, as the roughness template image provided by the image processing unit, an image for which image processing of emphasizing fluctuations in edge shape formed in a pattern is performed.

4. A scanning electron microscope according to claim 1, wherein:
   said image acquisition unit further includes an addressing image acquisition unit which acquires an addressing image having an addressing pattern formed on the sample; and said image processing unit further includes a coordinate acquisition unit which acquires coordinates of the addressing pattern by pattern matching between the addressing image acquired by the addressing image acquisition unit and an addressing template image to thereby acquire coordinates of the enlarged measurement area from the acquired coordinates of the addressing pattern;

wherein said image acquisition unit acquires the enlarged measurement image on the basis of the coordinates of the enlarged measurement area acquired by the coordinate acquisition unit.

5. A scanning electron microscope according to claim 1, wherein:

said measurement repeatability evaluation unit uses variation in dimensions or variation in shape for the number of times of measurement as said presented value in association with the change in dimensions or the change in shape for the number of times of measurement.

6. A scanning electron microscope according to claim 1, wherein:

in response to the change in dimensions or the change in shape for the number of times of measurement, said dimensions or said shape being measured over the number of times of measurement, said measurement repeatability evaluation unit determines a function model with the best fitting by performing a fitting process for a plurality of function models, and then presents the determined function model as the evaluation value of the measurement repeatability as the tool.

7. A scanning electron microscope according to claim 1, wherein:

in response to the change in dimensions or the change in shape for the number of times of measurement, said dimensions or said shape being measured over the number of times of measurement, said measurement repeatability evaluation unit determines a function model with the best fitting by performing a fitting process for a plurality of function models, and then calculates the deviation of the change in dimensions, or that of the change in shape, for the number of times of measurement, from the determined function model to present a value in response to the calculated deviation as the evaluation value of the measurement repeatability as the tool.

8. A scanning electron microscope according to claim 1, wherein:

in response to the change in dimensions or the change in shape for the number of times of measurement, said dimensions or said shape being measured over the number of times of measurement, said measurement repeatability evaluation unit determines a function model with the best fitting by performing a fitting process for a plurality of function models, and then calculates the deviation of the change in dimensions, or that of the change in shape, for the number of times of measurement, from the determined function model to present variation in said calculated deviation as the evaluation value of the measurement repeatability as the tool.

9. A scanning electron microscope according to claim 1, wherein:

said measurement repeatability evaluation unit also presents the imaging conditions used in the image acquisition unit as the evaluation value of the measurement repeatability as the tool.

10. A scanning electron microscope comprising:

an image acquisition unit which scans an electron beam on a sample under specified imaging conditions at each measurement over the number of times of measurement to acquire an enlarged measurement image at high magnification based on an electron signal emitted from the sample;

an image processing unit which acquires an enlarged measurement area image of a local area by using two-dimensional pattern matching with a roughness template image showing a micro-minute shape of a pattern in the local area, from the enlarged measurement image at high magnification acquired at each measurement over the number of times of measurement by the image acquisition unit; and a measurement unit which measures dimensions or a shape of the pattern in the enlarged measurement area on the basis of the enlarged measurement area image of the local area, which has been acquired at each measurement over the number of times of measurement by the image processing unit.

11. A scanning electron microscope according to claim 10, wherein:

said image acquisition unit further includes a roughness template image acquisition unit which acquires the roughness template image which is provided by the image processing unit, as the local area from the enlarged measurement image at high magnification acquired according to an electron signal emitted from a specified sample by scanning the electron beam on the specified sample.

12. A scanning electron microscope according to claim 10, wherein:

said image acquisition unit includes an addressing image acquisition unit which acquires an addressing image having an addressing pattern formed on the sample; and said image processing unit includes a coordinate acquisition unit which acquires coordinates of the addressing pattern by pattern matching between the addressing image acquired by the addressing image acquisition unit and an addressing template image to thereby acquire coordinates of the enlarged measurement area from the acquired coordinates of the addressing pattern;

wherein said image acquisition unit acquires the enlarged measurement image on the basis of the coordinates of the enlarged measurement area acquired by the coordinate acquisition unit.

13. A method for evaluating measurement repeatability of a scanning electron microscope, said method comprising:

an image acquisition step of scanning an electron beam on a sample under specified imaging conditions at each measurement over the number of times of measurement to acquire an enlarged measurement image at high magnification based on an electron signal emitted from the sample;

an image processing step of acquiring an enlarged measurement area image of a local area by using two-dimensional pattern matching with a roughness template image showing a micro-minute shape of a pattern in the local area, from the enlarged measurement image at high magnification acquired at each measurement over the number of times of measurement by the image acquisition step;

a measurement step of measuring dimensions or a shape of the pattern in the enlarged measurement area on the basis of the enlarged measurement area image of the local area, which has been acquired at each measurement over the number of times of measurement by the image processing step; and a measurement repeatability evaluation step of presenting, as an evaluation value of the measurement repeatability as a tool, a value associated with the change in dimensions or the change in shape for the number of times of measurement, said dimensions or said shape being measured over the number of times of measurement by the measurement step.

14. A method for evaluating measurement repeatability according to claim 13, wherein:

in said measurement repeatability evaluation step, said presented value in association with the change in dimensions or the change in shape for the number of times of measurement is variation in dimensions or variation in shape for the number of times of measurement.

15. A method for evaluating measurement repeatability according to claim 13, wherein:

said measurement repeatability evaluation step, in response to the change in dimensions or the change in shape for the number of times of measurement, said dimensions or said shape being measured over the number of times of measurement, determines a function model with the best fitting by performing a fitting process for a plurality of function models, and then presents the determined function model as the evaluation value of the measurement repeatability as the tool.

16. A method for evaluating measurement repeatability according to claim 13, wherein:

in response to the change in dimensions or the change in shape for the number of times of measurement, said dimensions or said shape being measured over the number of times of measurement, said measurement repeatability evaluation step determines a function model with the best fitting by performing a fitting process for a plurality of function models, and then calculates the deviation of the change in dimensions, or that of the change in shape, for the number of times of measurement, from the determined function model to present a value in response to the calculated deviation as the evaluation value of the measurement repeatability as the tool.

17. A method for evaluating measurement repeatability according to claim 13, wherein:

said measurement repeatability evaluation step also presents, as the evaluation value of the measurement repeatability evaluation value as the tool, the imaging conditions used in the image acquisition step.

* * * * *